(12) United States Patent
Luekenga et al.

(10) Patent No.: US 11,331,036 B2
(45) Date of Patent: May 17, 2022

(54) SYSTEMS FOR INTRAOPERATIVE NEUROPHYSIOLOGICAL MONITORING (71) Applicant: Neuromonitoring Associates, Inc., Las Vegas, NV (US)

(72) Inventors: Nick Luekenga, Henderson, NV (US); Scott F. Davis, Ocean Springs, MS (US)

(73) Assignee: Neuromonitoring Associates, Inc., Las Vegas, NV (US)

( * ) Notice: Subject to any disclaimer, the term of this patent is extended or adjusted under 35 U.S.C. 154(b) by 913 days.

(21) Appl. No.: 16/053,311

(22) Filed: Aug. 2, 2018

(65) Prior Publication Data
US 2019/0038169 A1 Feb. 7, 2019

Related U.S. Application Data

(60) Provisional application No. 62/540,868, filed on Aug. 3, 2017.

(51) Int. Cl.
 *A61B 5/375* (2021.01)
 *G06F 3/01* (2006.01)
 *A61B 5/00* (2006.01)
 *A61B 5/377* (2021.01)
 *A61B 5/389* (2021.01)

(52) U.S. Cl.
 CPC .............. *A61B 5/375* (2021.01); *A61B 5/377* (2021.01); *A61B 5/389* (2021.01); *A61B 5/704* (2013.01); *A61B 5/7445* (2013.01); *A61B 5/7455* (2013.01); *G06F 3/015* (2013.01); *A61B 2505/05* (2013.01)

(58) Field of Classification Search
 None
 See application file for complete search history.

(56) References Cited

U.S. PATENT DOCUMENTS

2014/0121555 A1* 5/2014 Scott .................. A61B 5/24
600/546

OTHER PUBLICATIONS

Alan David Kaye • Scott Francis Davis—Principles of Neurophysiological Assessment, Mapping, and Monitoring; ISBN 978-1-4614-8941-2; 2014; Chapter 1 pp. 1-10 (Year: 2014).*

* cited by examiner

*Primary Examiner* — Kaylee R Wilson
*Assistant Examiner* — Jay B Shah
(74) *Attorney, Agent, or Firm* — Kilpatrick Townsend & Stockton LLP (57) ABSTRACT

Systems, architectures, and methods of neurophysiological monitoring are described. In a particular example, an architecture may include a monitoring system and display system including two or more display devices. The monitoring system may manage the monitoring of some aspect of a patient's nervous system. A first display device is positioned adjacent the patient and viewable by a first user. A second display device is positioned apart from the patient and viewable by a second user and obscured from the first user. The first display device and the second display device may be used to display monitoring data collected by the monitoring system.

17 Claims, 8 Drawing Sheets

SYSTEMS FOR INTRAOPERATIVE NEUROPHYSIOLOGICAL MONITORING

CROSS-REFERENCES TO RELATED APPLICATIONS

This application claims the benefit of U.S. Provisional Application No. 62/540,868, filed Aug. 3, 2017, the entire contents of which are hereby incorporated by reference in its entirety for all purposes.

BACKGROUND

Intraoperative neurophysiological monitoring can be used to monitor aspects of a patient's nervous system during an operation such as a surgery. Such monitoring may be particularly useful when the operation involves the nervous system itself or which could pose a risk to its anatomic or physiologic integrity. A computer system is attached to the patient's nervous system using one or more electrodes. The computer system controls input electrical signals provided to the nervous system, captures electrical signals registered at the nervous system (e.g., certain signals generated in response to the input electrical signals), and provides the captured electrical signals for presentation (e.g., on a monitor).

BRIEF SUMMARY

Various examples are described relating to systems for intraoperative neurophysiological monitoring and techniques thereof.

In an example, a system is described. The system includes a controller including interfaces for connecting with one or more attachment devices. The controller is configured to generate a stimulation signal that is deliverable to a subject via the one or more attachment devices. The controller is also configured to receive neurological data via the one or more attachment devices. The neurological data is generated at least in part by the subject in response to the stimulation signal being delivered to the subject. The system also includes a first display device positionable at a first position adjacent to the subject such that the first display device is viewable by a first user and a second user when positioned at the first position. The first display device is configured to display a first representation of the neurological data. The system also includes a second display device positionable at a second position offset from the subject such that the second display device is viewable by the second user and obscured from the first user when positioned at the second position. The second display device is configured to display the first representation of the neurological data or a second representation of the neurological data. The first user is different from the second user at least with respect to respective responsibilities to the subject. The system also includes a computing device electronically coupled with the controller and the first and second display devices. The computing device includes a memory and a processor configured to generate the first representation of the neurological data and the second representation of the neurological data. The computing device is also configured to send the first representation of the neurological data to the first display device for presentation to the first user. The computing device is also configured to send the first representation of the neurological data or the second representation of the neurological data to the second display device for presentation to the second user.

In yet another example, an architecture for neurophysiological monitoring of a human subject is described. The architecture includes a monitoring system configured to employ one or more electrophysiological modalities to monitor neural structures of the human subject when a surgical operation is performed on the human subject. The architecture also includes a display system including a first display device positioned at a first position adjacent to the human subject such that the first display device is viewable by a first user when the first user is performing the surgical operation on the human subject. The first display device is configured to display first monitoring data based on data output by the monitoring system. The display system also includes a second display device positioned at a second position offset from the human subject such that the second display device is viewable by the second user and obscured from the first user when the first user is performing the surgical operation on the human subject. The second display device is configured to display the first monitoring data or second monitoring data based on data output from the monitoring system. The first user is different from the second user at least with respect to responsibilities of the first user and the second user to the human subject during the surgical operation.

In yet another example, a computer-implemented method is described. The method includes instructing a controller to initiate an electrophysiological monitoring routine on a nervous system of a patient. The method also includes receiving output signal data from the controller. The output signal data includes at least one of a triggered electrophysiological signal detected at the nervous system of the patient or a spontaneous electrophysiological signal detected at the nervous system of the patient. The method also includes generating a plurality of user interface elements based at least in part on the output signal data. The method also includes providing a first user interface element of the plurality of user interface elements for presentation at a first display device. The first display device is positioned at a first position such that a first user can view the first display device while physically interacting with the patient. The method also includes providing a second user interface element of the plurality of user interface elements for presentation at a second display device. The second display device is positioned at a second position such that a second user can view the second display device and view the first display device. Other examples include corresponding computer systems, apparatus, and computer programs recorded on one or more computer storage devices, each configured to perform the actions of the methods.

BRIEF DESCRIPTION OF THE DRAWINGS

Various examples in accordance with the present disclosure will be described with reference to the drawings, in which.

DETAILED DESCRIPTION

In the following description, various examples will be described. For purposes of explanation, specific configurations and details are set forth in order to provide a thorough understanding of the examples. However, it will also be apparent to one skilled in the art that the examples may be practiced without the specific details. Furthermore, well-known features may be omitted or simplified in order not to obscure the example being described.

Examples herein are directed systems and techniques for intraoperative neurophysiological monitoring, and in particular, to approaches for positioning display devices for contemporaneously presenting monitoring data (e.g., information about a patient's nervous system) to users (e.g., medical professionals) in an operating environment (e.g., surgical bay, operating room, an exam room, and any other suitable environment in which operations can be performed). The different display devices may be arranged to be viewable by certain users and obscured from other users. Moreover, the monitoring data displayed on the different display devices can be tailored to the particular user or set of users who will view the display devices. In this manner, the described system manages access to the monitoring data (e.g., by the positioning of the different display devices) and arrangement of the actual monitoring data (e.g., by tailoring what is presented based on user roles.

Unlike other systems that require a first user (e.g., a surgeon) to rely entirely on verbal queues from a second user (e.g., a trained and clinically certified technologist) who interprets monitoring data about a nervous system of a patient, the systems described herein enable presentation of real-time monitoring data to all or many of the users in the operating environment. This, of course, is in addition to any verbal or other types of queues that the technologist may wish to provide to the surgeon based on the technologist's interpretation of the monitoring data. Thus, the surgeon can see and hear real-time feedback relating to how her actions during the operation are impacting the nervous system of her patient. Having this additional feedback channel allows the surgeon to more confidently perform the operation, resulting in better patient outcomes. When the second user is a trained and clinically certified technologist, as opposed to a sales representative or other uncertified user, the information shared by the technologist with the surgeon via a display device and/or verbally will be more medically relevant and useful to the surgeon. This is because the trained and clinically certified technologist not only has an understanding of how the monitoring system operates, but also has an understanding of how the systems of the patient's body should function and how they may change given conditions of the surgery.

Turning now to a particular example, in this example, a neurophysiological monitoring system includes a monitoring system and a display system. The monitoring system is configured to monitor aspects of a patient's nervous system during some predetermined period such as during a surgical operation. To this end, the monitoring system includes components for electrical signal generation, electrical signal detection, electrical signal processing and filtering, and electrical signal presentation. The display system is configured to display information output from the monitoring system. To this end, the display system includes at least a first display device and second display device coupled to a computer of the monitoring system. The first display device is positioned at a first position in an operating environment. For example, the first display device can be positioned adjacent to an operating bed so as to be visible by a surgeon who will operate on a patient in the operating bed. The second display device is positioned at a second position in the operating environment. For example, the second display device can be positioned offset from the operating bed so as to be visible by a technologist who will be primarily responsible for operating the neurophysiological monitoring system. The second display device may be obscured from the view of the surgeon. This may be desirable in order to focus the surgeon's attention on information presented on the first display device, which may be different from information presented on the second display device. In addition, with the technologist having a view of both display devices, she can decide how best to share information with the surgeon about the monitoring. For example, if the technologist can see that surgeon is looking at the first display device, the technologist can cause messages or other information to be presented at the first display device. If, on the other hand, the technologist sees that the surgeon is not looking at the first display device, the technologist can share an audible message, either verbally or using a generated sound.

Figure 1:
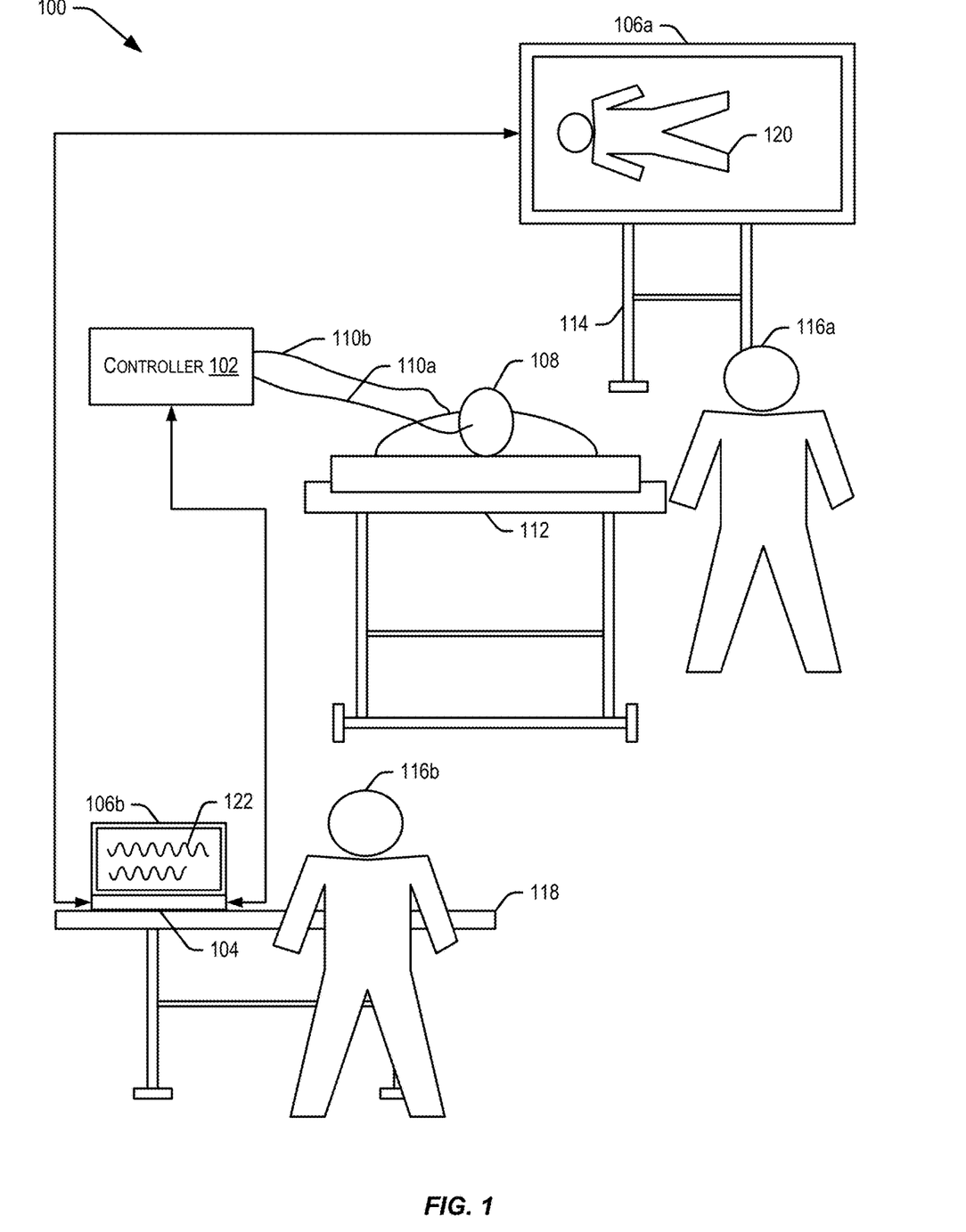
FIG. 1 illustrates an example neurophysiological monitoring system implemented in an operating environment, according to at least one example.

Turning now to the figures, FIG. 1 illustrates an example neurophysiological monitoring system 100, according to at least one example. The neurophysiological monitoring system 100 includes a monitoring system including a controller 102 and a computing device 104, and a display system including a first display device 106a and a second display device 106b. The controller 102 and the display devices 106 may be electronically connected to the computing device 104 in any suitable manner (e.g., network cables, wireless networks, optical cables, power cables, input/output interfaces, etc.).

Generally, the computing device 104, which may be any suitable computing device, is configured to manage the operation of the controller 102 and generate and provide information for presentation at the display devices 106a, 106b. The controller 102, operating under at least partial control of the computing device 104, may be configured to generate, deliver, detect, and/or process electrical signals with respect to a patient 108. Thus, the controller 102 is an example of a multimodality machine for simultaneous signal generation, detection, and recording. Such signals may be referred to as neurological data or electrophysiological data. In some examples, the controller 102 may receive commands from the computing device 104 to send electrical signals to the patient 108. Response signals may be detected or generated by the patient 108 in response to electrical signals from the controller 102. These response signals are passed by the controller 102, which may perform some filtering and/or processing, to the computing device 104. The computing device 104, executing monitoring modules (e.g., dedicated hardware, firmware, or software), may be configured to receive, augment, and/or otherwise process the response signals prior to providing representations of the response signals for presentation at the display devices 106. The modules of the computing device 104 may be enable simultaneous viewing of multiple tests. In some examples, the tests are viewed on the second display device 106b and/or the first display device 106a. In some examples, the second display device 106b is considered a primary display device on which is viewed a primary set of tests. The first display device 106b may be considered a secondary display device on which is viewed a subset of the primary set of tests or a different set altogether (e.g., a secondary set).

The electrical signals may be delivered from the controller 102 to the patient 108 and received from the patient 108 via one or more electrodes 110a, 110b. The electrodes 110 may be any suitable electrical lead that can be placed in electrical communication with the patient's 108 nervous system. The types of electrodes 110 used and their placement on the patient 108 may be specific to the type of neurophysiological monitoring being performed by the neurophysiological monitoring system 100. For example, when the neurophysiological monitoring includes evoked potential monitoring, a first electrode 110a may be placed near the patient's 108 spinal cord and a second electrode 110b may be placed near a peripheral nerve in the patient's 108 ankle. The monitoring may occur as electrical signals are introduced at the second electrode 110b and then detected by the first electrode 110a.

When the neurophysiological monitoring system 100 is implemented in an operating environment, the patient 108 may be placed on an operating table 112. The operating table 112 may be fixed or mobile, and may include adjustability. In some examples, the operating table 112 may be specifically adapted for neurophysiological monitoring. For example, the operating table 112 may include grounding connections, adapters for holding or otherwise supporting the electrodes 110 and/or components of the controller 102 described with reference to other figures.

The first display device 106a may be positioned adjacent to the operating table 112 or in some other manner adjacent to the patient 108. For example, the first display device 106a may be supported by a frame 114 that is movable to be positioned adjacent to the operating table 112 and/or fixed at a location adjacent to the operating table 112. The frame 114, in some examples, may be used to mount the first display device 106a to a wall, a ceiling, or a floor in the operating environment. The frame 114 may also include some degree of adjustability. For example, the frame 114 may include a mechanism such as an adjustable television mount to provide one or more degrees of adjustability (e.g., vertical, horizontal, in and out, rotate right and left, and/or rotate up and down).

In some examples, the positioning of the first display device 106a may be relative to a first user 116a such as surgeon. For example, the first display device 106a may be positioned such that a display surface of the first display device 106a is viewable (e.g., within a field of view) of the first user 116a. This may enable the first user 116a to attend to the patient 108 while also viewing the first display device 106a.

The second display device 106b may be positioned away from the operating table 112 or in some other manner offset from the first user 116a and the patient 108. For example, the second display device 106b may be supported by a table 118 positioned behind or to the side of the operating table 112. The table 118 may be moveable or fixed with respect to the operating table 112. In some examples, the second display device 106b may be electronically and physically connected to the computing device 104. For example, the computing device 104 may be a laptop and the second display device 106b may be a monitor of the laptop.

In some examples, the positioning of the second display device 106b may be relative to a second user 116b such as a clinically trained and certified technologist. For example, the second display device 106b may be positioned such that a display surface of the second display device 106b is viewable (e.g., within a field of view) of the second user 116b, but not within the field of view of the first user 116a. This may enable the second user 116b to simultaneously view both the first display device 106a and the second display device 106b.

In some examples, the information presented on the first display device 106a may be different from the information presented on the second display device 106b. For example, on the first display device 106a may be presented a simplified representation 120 of the response signals detected by the controller 102. And on the second display device 106b may be presented a more comprehensive representation 122 of the response signals. This may be desirable to give the second user 116b, who has received specialized training in neurophysiological monitoring methods, a more complete view of the neurophysiological monitoring being performed on the patient 108. Giving the first user 116a the simplified representation 120 may be desirable to avoid the first user 116a from being overwhelmed by the neurophysiological monitoring data. The representations 120, 122 are examples of what may be presented, but it should be understood that any suitable representation of the response signals may be generated by the computing device 104 and provided for presentation on the display devices 106. In some examples, the information presented on the display devices 106 is the same, e.g., in a screen sharing or desktop sharing example.

Figure 2:
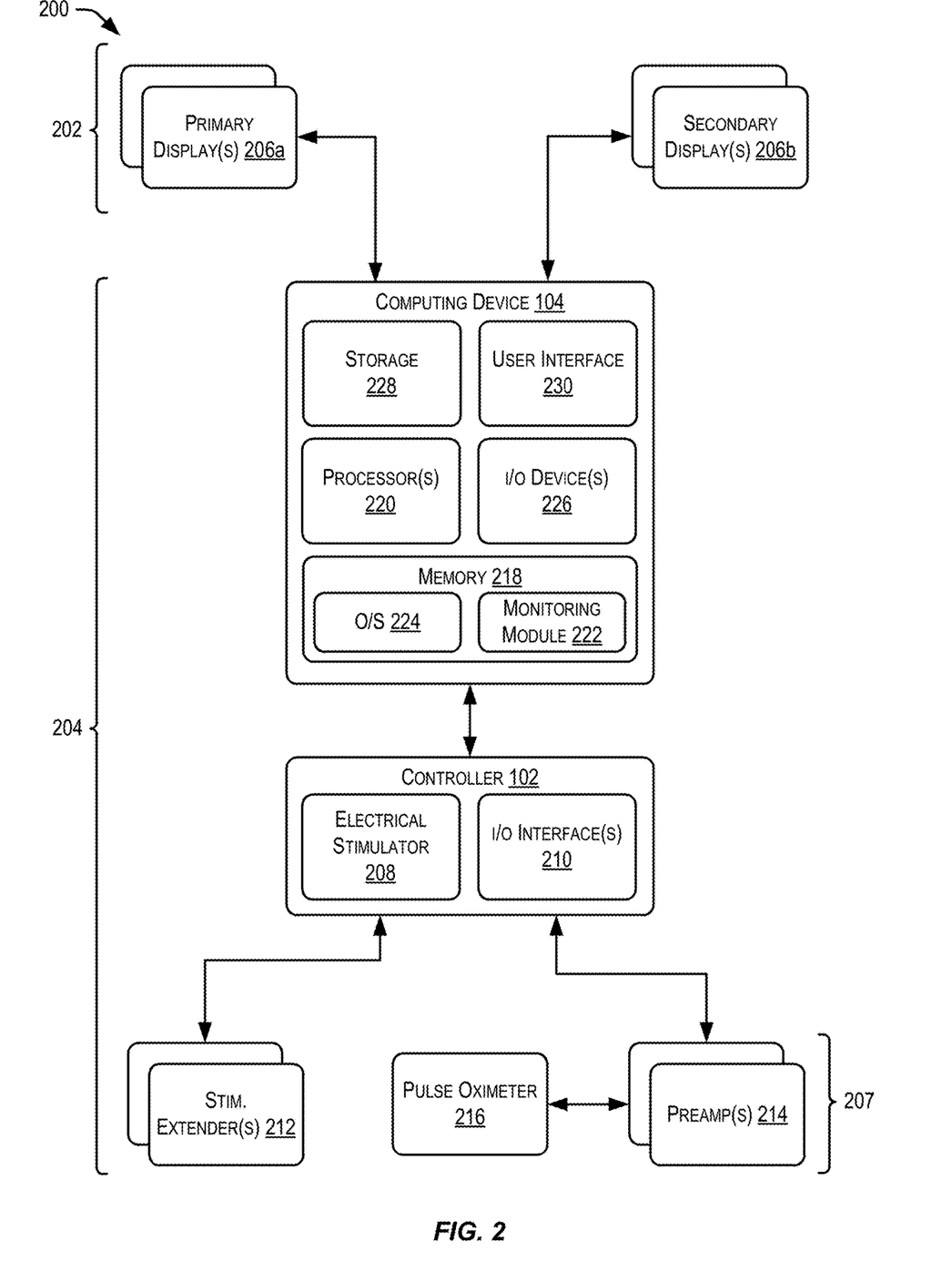
FIG. 2 illustrates a block diagram depicting components of an example neurophysiological monitoring system, according to at least one example.

FIG. 2 illustrates components of an example neurophysiological monitoring system 200, according at least one example. The neurophysiological monitoring system 200 is an example of the neurophysiological monitoring system 100 described herein. Thus, the neurophysiological monitoring system 200 includes a display system 202 and a monitoring system 204. Like the display system described with reference to FIG. 1, the display system 202 includes one or more display devices such as primary display device devices 206a and secondary display device devices 206b. Like the display devices 106, the display devices 206 may be any suitable device capable of visually presenting information. Examples of such devices may include cathode ray tube (CRT) displays, light-emitting diode (LED) displays, electroluminescent displays (ELD), electronic paper, plasma display panels (PDP), liquid crystal displays (LCD), organic light-emitting diode (OLED) displays, surface-conduction electron-emitter displays (SED), field emission displays (FED), projectors (LCD, CRT, digital light processing (DLP), liquid crystal on silicon (LCoS), LED, hybrid LED, laser diode), and any other suitable device capable of displaying information.

The primary display devices 206a may be positioned adjacent to the second users 116b. The secondary display devices 206b may be positioned adjacent to the first users 116a.

The monitoring system 204 is an example of the monitoring system described with reference to FIG. 1. Examples of suitable monitoring systems 204 may include the NIM-ECLIPSE® E4 nerve monitoring system sold by MEDTRONIC® BV and the AXON ECLIPSE® never monitoring system. To this end, the monitoring system 204 may include the computing device 104, the controller 102, and one or more attachment devices 207. The attachment devices 207 may be connected to the controller 102 in order to augment or otherwise enable certain functions of the controller 102. In some examples, the attachment devices 207 are themselves separate modules that are disposed between the controller 102 and the patient 108. The function of the example attachment devices 207 will be discussed later. Though a few examples of attachment devices 207 are illustrated, other and different attachment devices 207 may also be connected to the controller 102.

The controller 102 may include an electrical stimulator 208 and one or more input/output interfaces 210. The electrical stimulator 208 may include a wide variety of triggering modes and pulse outputs to provide electrical stimulation for a variety of components of a human nervous system (e.g., peripheral, direct nerves, cortical, transcranial, and other suitable components). The techniques described herein may also be applied to other non-human mammals. One or more stimulation extenders 212 may be connected to the electrical stimulator 208 via one or more of the input/output interfaces 210. To the stimulation extenders 212 may be connected one or more of the electrodes 110. The stimulation extenders 212 may be placed near the patient 108.

The attachment devices 207 also include one or more preamplifiers 214. The preamplifiers 214 are examples of digital preamplifier modules. In some examples, the preamplifiers 214 provide signal detection, amplification, montage selection, A/D conversion, antialiasing filtering, and digital signal processing. The preamplifiers 214 may route detected signals to the controller 102 via any suitable connection. Each preamplifier 214 may include inputs for the electrodes 110 and/or a pulse oximeter 216. The preamplifiers 214 may be used at different patient locations in order to achieve the desired neurophysiological monitoring.

The pulse oximeter 216 may be connected to the controller 102 via one of the preamplifiers 214. The pulse oximeter may be used to measure oxygen saturation information of the patient 108.

The computing device 104 may be in communication with the other components of the neurophysiological monitoring system 200 via one or more network(s), wired connections, and the like. The network may include any one or a combination of many different types of networks, such as cable networks, the Internet, wireless networks, cellular networks, radio networks, and other private and/or public networks.

Turning now to the details of the computing device 104, the computing device 104 may include at least one memory 218 and one or more processing units (or processor(s)) 220. The processor(s) 220 may be implemented as appropriate in hardware, computer-executable instructions, software, firmware, or combinations thereof. For example, the processors 220 may include one or more general purpose computers, dedicated microprocessors, or other processing devices capable of communicating electronic information. Examples of the processors 220 include one or more application-specific integrated circuits (ASICs), field programmable gate arrays (FPGAs), digital signal processors (DSPs) and any other suitable specific or general purpose processors.

Computer-executable instruction, software, or firmware implementations of the processor(s) 220 may include computer-executable or machine-executable instructions written in any suitable programming language to perform the various functions described. The memory 218 may include more than one memory and may be distributed throughout the computing device 104. The memory 218 may store program instructions (e.g., a monitoring module 222) that are loadable and executable on the processor(s) 220, as well as data generated during the execution of these programs. Depending on the configuration and type of memory including the monitoring module 222, the memory 218 may be volatile (such as random access memory (RAM)) and/or non-volatile (such as read-only memory (ROM), flash memory, or other memory). The computing device 104 may also include additional removable storage 228 and/or non-removable storage including, but not limited to, magnetic storage, optical disks, and/or tape storage. The disk drives and their associated computer-readable media may provide non-volatile storage of computer-readable instructions, data structures, program modules, and other data for the computing devices. In some implementations, the memory 218 may include multiple different types of memory, such as static random access memory (SRAM), dynamic random access memory (DRAM), or ROM. The memory 218 may also include an operating system 224.

The memory 218 and the additional storage 228, both removable and non-removable, are examples of computer-readable storage media. For example, computer-readable storage media may include volatile or non-volatile, removable, or non-removable media implemented in any suitable method or technology for storage of information such as computer-readable instructions, data structures, program modules, or other data. As used herein, modules may refer to programming modules executed by computing systems (e.g., processors) that are part of the monitoring module 222. The modules of the monitoring module 222 may include one or more components, modules, and the like. The computing device 104 may also include input/output ("I/O") device(s) and/or ports 226, such as for enabling connection with a keyboard, a mouse, a pen, a voice input device, a touch input device, a display, speakers, a printer, or other I/O device. The I/O device(s) 226 may enable communication with the other systems of the neurophysiological monitoring system 200.

The computing device 104 may include a user interface 230. The user interface 230 may be utilized by an operator or other authorized user such as the second user 116b to access portions of the computing device 104 (e.g., the monitoring module 222). In some examples, the user interface 230 may include a graphical user interface, web-based applications, programmatic interfaces such as application programming interfaces (APIs), or other user interface configurations.

Figure 3:
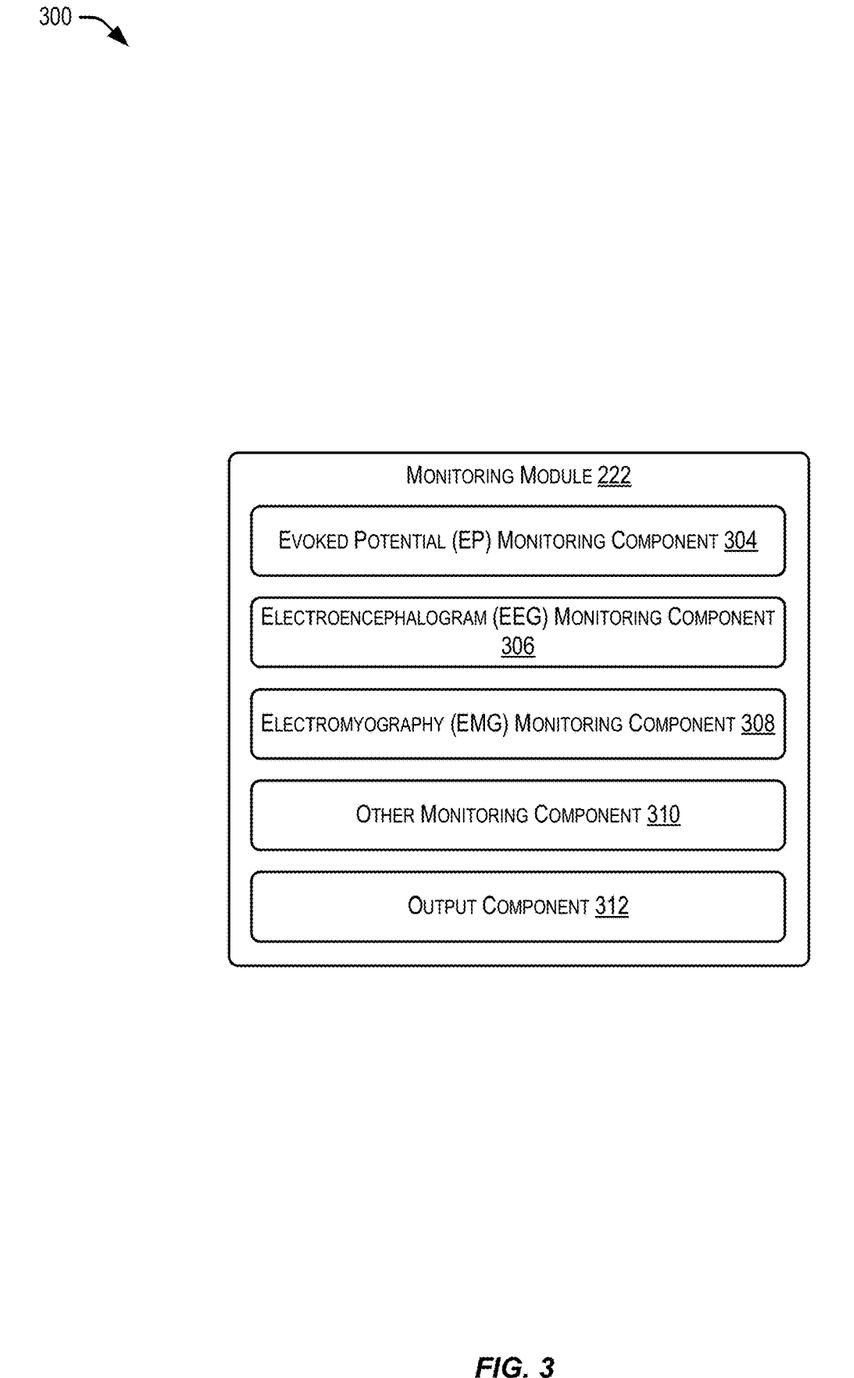
FIG. 3 illustrates an example device for implementing techniques relating to intraoperative neurophysiological monitoring, according to at least one example.

FIG. 3 illustrates an example device 300 including the monitoring module 222, according to at least one example. The monitoring module 222 may be configured to manage one or more sub-modules, components, engines, and/or services directed to examples disclosed herein. For example, the monitoring module 222 includes an evoked potential (EP) monitoring component 304, an electroencephalogram (EEG) monitoring component 306, an electromyography (EMG) monitoring component 308, other monitoring component 310 (e.g., electroencephalography monitoring), and an output component 312. While these modules are illustrated in FIG. 3 and will be described as performing discrete tasks with reference to the flow charts, it is understood that FIG. 3 illustrates example configurations and other configurations performing other tasks and/or similar tasks as those described herein may be implemented according to the techniques described herein. Other modules, components, engines, and/or services may perform the same tasks as the monitoring module 222 or other tasks. Each module, component, or engine may be implemented in software, firmware, hardware, and in any other suitable manner.

Generally, the EP monitoring component 304 may be configured to manage monitoring techniques that rely on evoked potentials (e.g., sensory and motor).

Generally, the EEG monitoring component 306 may be configured to manage monitoring techniques that rely on electroencephalograms.

Generally, the EMG monitoring component 308 may be configured to manage monitoring techniques that rely on electromyography.

Generally, the other monitoring component 310 may be configured to manage monitoring techniques that rely on approaches other than EP monitoring, EEG monitoring, and/or EMG monitoring.

Generally, the output component 312 may be configured to generate user interface elements and other representations of output signals to be output to the display devices for display.

Figure 4:
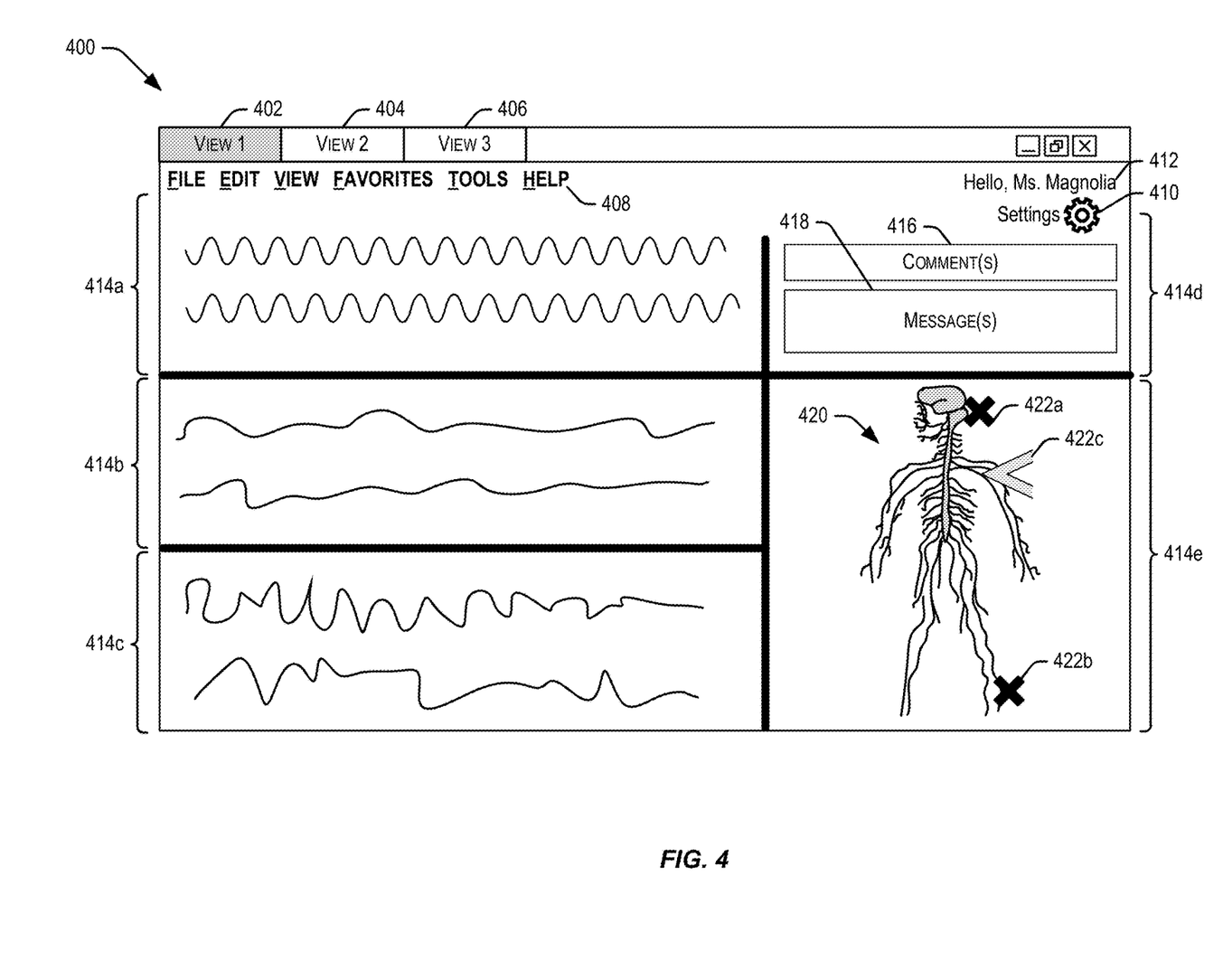
FIG. 4 illustrates an example view of a user interface depicting user interface elements relating to intraoperative neurophysiological monitoring, according to at least one example.
Figure 5:
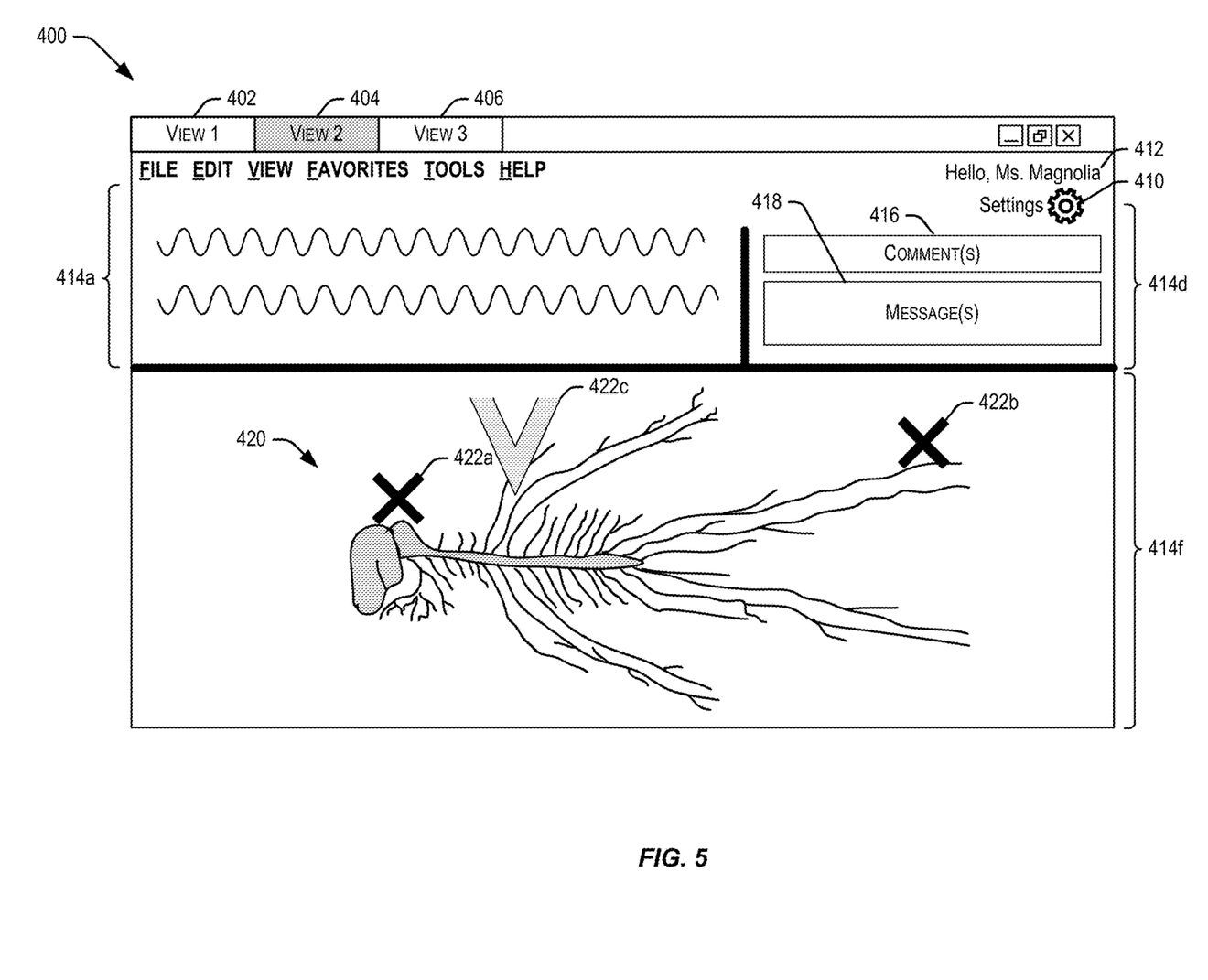
FIG. 5 illustrates an example view of a user interface depicting user interface elements relating to intraoperative neurophysiological monitoring, according to at least one example.
Figure 6:
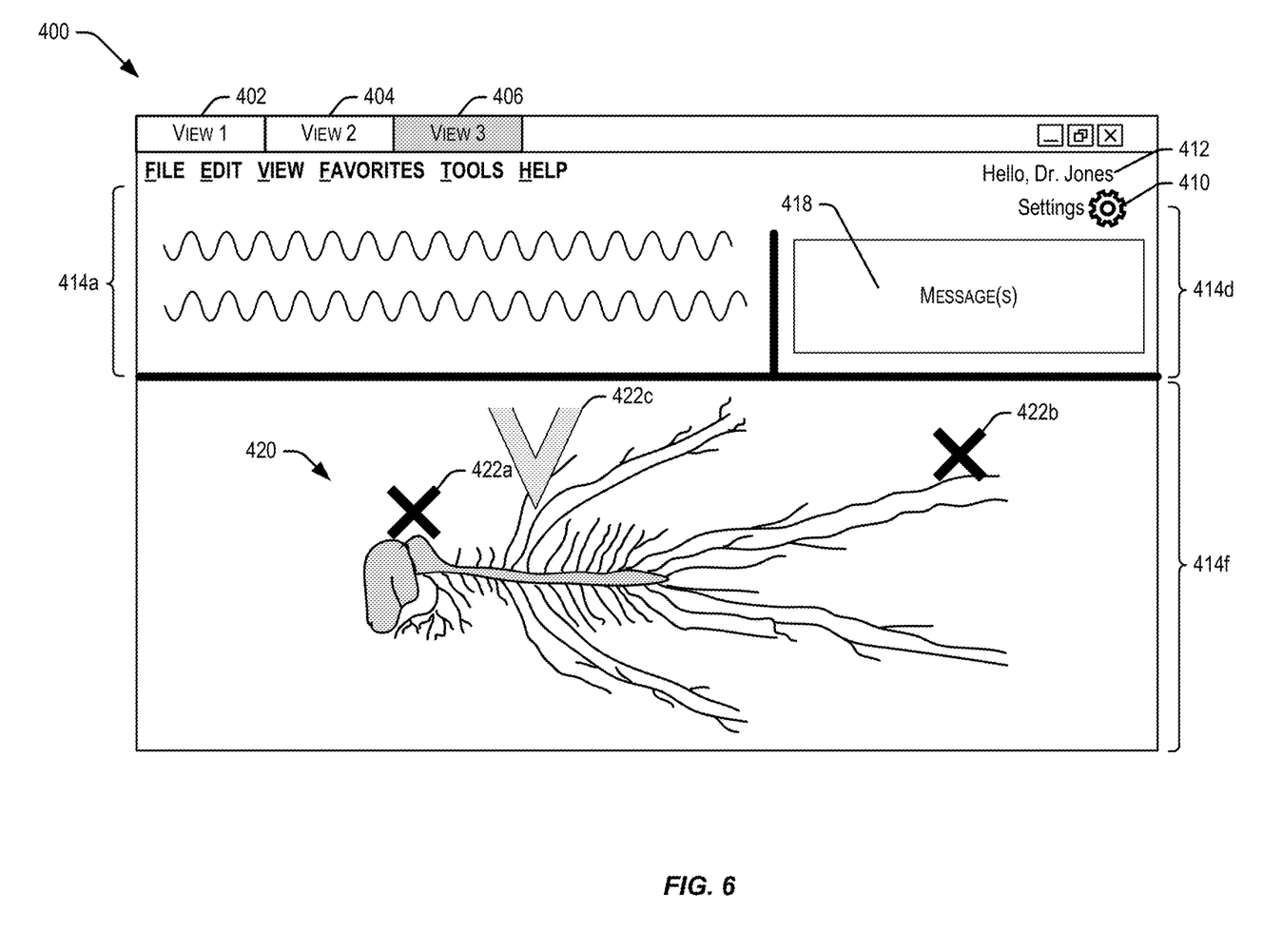
FIG. 6 illustrates an example view of a user interface depicting user interface elements relating to intraoperative neurophysiological monitoring, according to at least one example.

FIGS. 4-6 illustrates examples views 402-406 of an example user interface 400 that may be used to present monitoring data, according to at least one example. The user interface 400 may be generated by the output component 312 and presented on the display devices 206.

FIG. 4 depicts a first view 402 of the user interface 400. In some examples, more than three views are provided by the user interface 400. The views 402-406 may be used to convey the same information differently or to convey different information. For example, the first view 402 may be an example of a view that is suitable for presentation to the second user 116b. This may be appropriate because the first view 402 includes information that the second user 116b can interpret, but which may be difficult for interpretation by the first user 116a.

Generally, the user interface 400 may include a tool bar 408 and a settings adjuster 410. The tool bar 408 may be used to access functions of the monitoring module 222. The settings adjuster 410 may be used to adjust settings of the user interface 400. For example, the settings may be customized or otherwise tailored to a particular user such as user "Ms. Magnolia" 412. When a different user logs in to the device, a different user may be represented instead of Ms. Magnolia.

The first view 402 may be divided into a plurality of areas 414a-414e. Within each area 414 may be presented different information relating to a neurophysiological monitoring session. For example, the areas 414a-414c may include wave form data that represents stimulation signals and/or response signals detected at the patient 108. The wave form data are examples of user interface elements that can be generated and presented in the user interface 400.

The area 414d may include a comment field 416 and a message field 418. The comment field 416 may be used by the user 116 to make comments about the wave form data or other aspects of the monitoring session. The comments can be associated with a time stamp. The message field 418 may be used by the user 116 to send messages to other connected devices and/or display devices. For example, the second user 116b may input a message into the message field 418 while viewing the user interface 400 on a primary display device. The message can be transmitted to a secondary display device viewable by the first user 116a. The first user 116a, in some examples, may include an input device in order to send a reply message back to the second user 116b. The comment field 416 and the message field 418 are examples of user interface elements that can be generated and presented in the user interface 400.

The area 414e may include a graphical representation 420 of a nervous system of the patient 108. The graphical representation 420 may identify any suitable feature of the nervous system together with other systems of the patient's 108 body (e.g., skeletal, muscular, cardiovascular, lymphatic, respiratory, endocrine, urinary, reproductive, digestive, etc.). The graphical representation 420 may also include other graphical indicators 422a-422N that correspond to aspects of the monitoring session. For example, the graphical indicators 422a and 422b represent locations where electrodes have been placed in the patient's 108 body. The graphical indicator 422c is used to draw attention a particular location of the patient's 108 body. For example, the graphical indicator 422c may identify an area of concern given an analysis of the monitoring data. The graphical representation 420 and the graphical indicators 422 are examples of user interface elements that can be generated and presented in the user interface 400.

As illustrated in FIG. 5, the second view 404 may be divided into a plurality of areas 414a, 414d, and 414f. Within each area 414 may be presented different information relating to a neurophysiological monitoring session. For example, the areas 414a and 414d may be configured to display information similar as described with reference to FIG. 4.

The area 414f can include similar information as the area 414e. In some examples, the larger view of the graphical representation 420 displayed in the view 404 may be desirable for the second user 116b when the second user 116b wants to focus on the location specific data provided by the graphical representation 420.

As illustrated in FIG. 6, the third view 406 may be divided similarly as the second view 404. Within each area 414 may be presented different information relating to a neurophysiological monitoring session. For example, the area 414a may be configured to display information similar as described with reference to FIG. 4. In the area 414d may be displayed the message field 418 alone. This may be because the third view 406 is tailored to a user named Dr. Jones. Dr. Jones may have updated his settings to remove the comment field 416. This may be desirable because Dr. Jones may be an example of the first user 116a, who may be uninterested in logging comments about the monitoring. Instead, Dr. Jones may be more interested in receiving messages from the second user 116b relating to the monitoring session.

The area 414f in the third view 406 can be formatted similarly as the area 414f in the second view 404. In some examples, the larger view of the graphical representation 420 displayed in the third view 406 may be desirable for the first user 116a when the first user 116a wants to focus on the location specific data provided by the graphical representation 420. This may be because the first user 116a is more interested in high level information as opposed to the more granular information provided by the wave form data in the areas 414a-414c.

Figure 7:
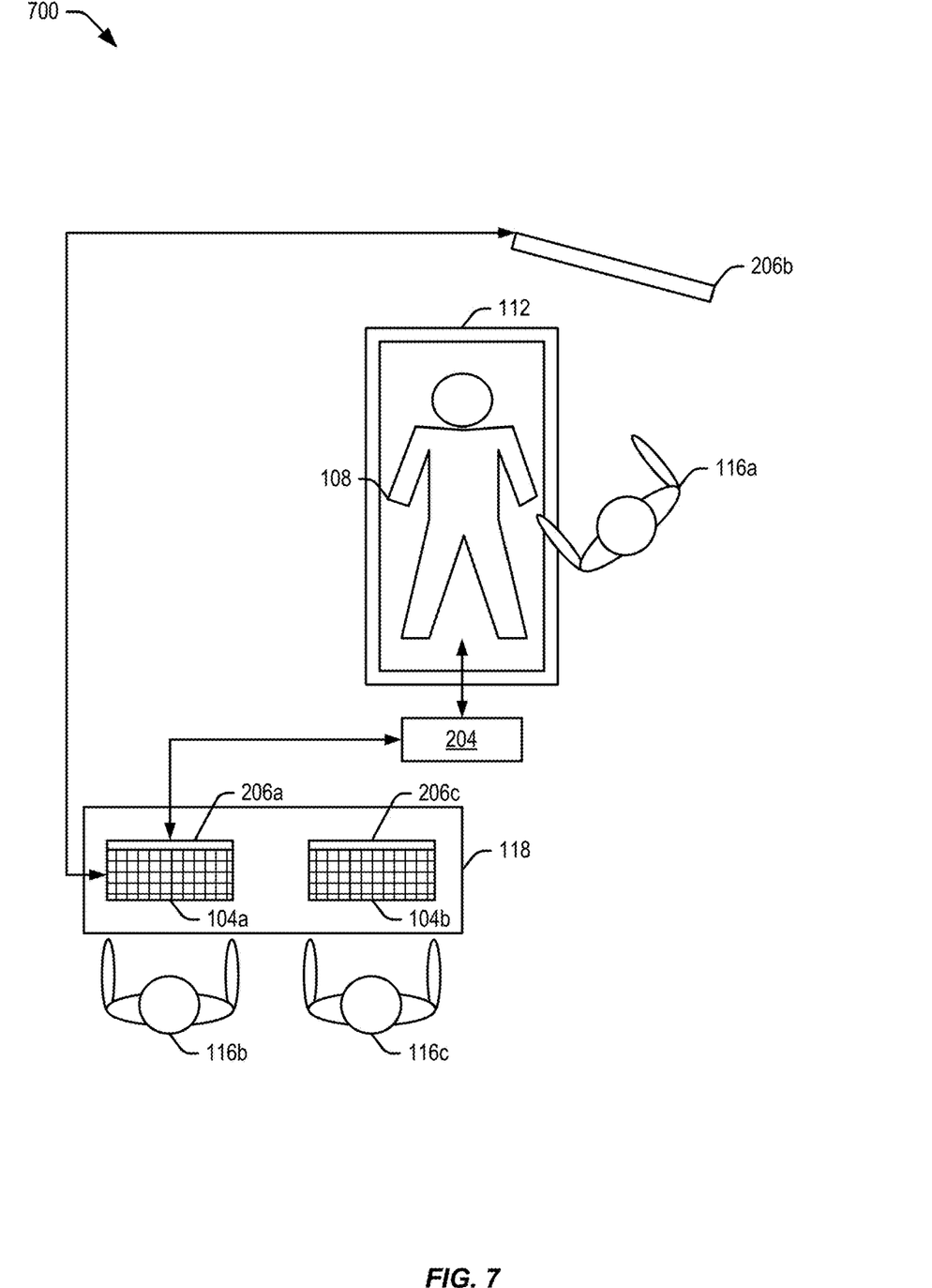
FIG. 7 illustrates an example neurophysiological monitoring system implemented in an operating environment, according to at least one example.

FIG. 7 illustrates an example system 700 depicting an example arrangement for neurophysiological monitoring, according to at least one example. FIG. 7 illustrates a top view of the system 700 including components previously described herein with reference to other figures. For example, the system 700 includes a secondary display device 206b positioned adjacent to the operating table 112.

In particular, the secondary display device 206b is rotated slightly with respect to the operating table 112. This may enable the first user 116a (e.g., a surgeon) to attend to the patient 108 on the operating table 112 while simultaneously viewing the secondary display device 206b.

The system 700 also includes a primary display device 206a positioned on the table 118. The primary display device 206a, in this example, is a monitor portion of the computing device 104a (e.g., a laptop computer). The primary display device 206a may be viewable by the second user 116b, but not the first user 116a.

The primary display device 206a may be primary with respect to the secondary display device 206b at least because the primary display device 206a may be used to present primary information and the second display device 206b may be used to present secondary information or a secondary version of the primary information. For example, on the primary display device 206a may be presented a monitoring data a very granular level, which can be interpreted by a technologist trained and certified in the field of neurophysiological monitoring. On the secondary display device 206b may be presented a simplified version of the monitoring data that is more appropriate for an individual who is untrained in the field of neurophysiological monitoring.

The information displayed on the two display devices 206 may be based on the same monitoring data obtained by the monitoring system 204 or may be based on different monitoring data obtained by the controller. The monitoring data may be included in user interface elements that are generated by the computing device 104. Thus, the user interface elements for the two display devices 206 can be generated based on the same monitoring data and/or different monitoring data. In some examples, a first user interface element is generated based on first monitoring data for the primary display device 206a and a version of the first user interface element is generated based on the first monitoring data for the secondary display device 206b. In some examples, a second interface element is generated based on second monitoring data for the primary display device 206a and a third interface element is generated based on the second monitoring data for the secondary display device 206b.

The system 700 may also include a second computing device 104b including a second secondary display device 206c. The second secondary display device 206c may also be positioned on the table 118. The second secondary display device 206c may be viewable by a third user 116c. In some examples, the second computing device 104b is useable by the third user 116c to perform additional or different monitoring of the patient 108. For example, the third user 116c may be an anesthesiologist who uses the second computing device 104c to monitor the effects of certain drugs on systems of the patient 108. This may include monitoring vital signs of the patient 108. In some examples, the second secondary display device 206c may be used to present user interface elements relating to the monitoring performed by the second computing device 104b. In some examples, the second secondary display device 206c may be used to present monitoring data collected by the monitoring system 204. In this manner, the second secondary display device 206c can be used in a similar manner to the secondary display device 206b.

Figure 8:
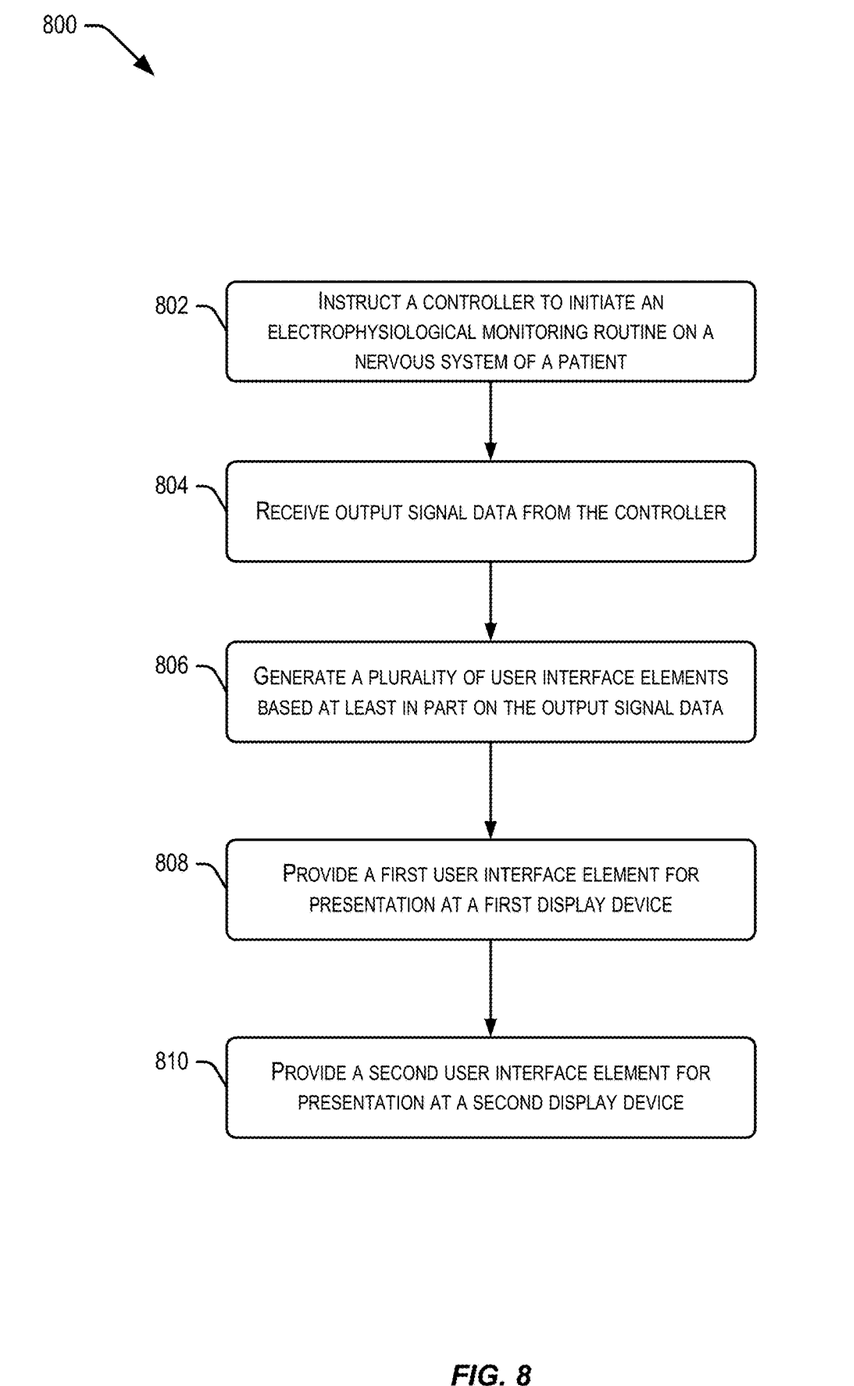
FIG. 8 illustrates a flow diagram depicting example acts for implementing techniques relating to intraoperative neurophysiological monitoring, according to at least one example.

FIG. 8 illustrates a flow diagram depicting a process 800 for implementing techniques relating to neurophysiological monitoring techniques, according to at least one example. The monitoring module 222 (FIG. 2) may perform the process 800 of FIG. 8. The process 800 is illustrated as logical flow diagram, each operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be omitted or combined in any order and/or in parallel to implement the processes.

Additionally, some, any, or all of the processes may be performed under the control of one or more computer systems configured with executable instructions and may be implemented as code (e.g., executable instructions, one or more computer programs, or one or more applications) executing collectively on one or more processors, by hardware, or combinations thereof. As noted above, the code may be stored on a computer-readable storage medium, for example, in the form of a computer program comprising a plurality of instructions executable by one or more processors. The computer-readable storage medium is non-transitory.

The process 800 may begin at 802 by instructing a controller to initiate an electrophysiological monitoring routine on a nervous system of the patient. This may be performed by one of the monitoring components 304-310 (FIG. 3).

At 804, the process 800 may include receiving output signal data from the controller. This may be performed by one of the monitoring components 304-310 (FIG. 3). The output signal data may include at least one of a triggered electrophysiological signal detected at the nervous system of the patient or a spontaneous electrophysiological signal detected at the nervous system of the patient.

At 806, the process 800 may include generating a plurality of user interface elements based at least in part on the output signal data.

At 808, the process 800 may include providing a first user interface element of the plurality of user interface elements for presentation at a first display device. This may be performed by the output component 312 (FIG. 3). In some examples, the first display device may be positioned at a first position such that a first user can view the first display device while physically interacting with the patient. In some examples, the first user interface element may include a representation of a portion of the output signal data with respect to graphical depiction of a generic nervous system.

At 810, the process 800 may include providing a second user interface element of the plurality of user interface elements for presentation at a second display device. This may be performed by the output component 312. In some examples, the second display device may be positioned at a second position such that a second user can view the second display device and view the first display device. In some examples, the second position may be located with respect to the patient in a manner the prohibits the second user from physically interacting with the patient.

The process 800 may also include generating an audible signal based at least in part on the output signal data. In this example, the process 800 may also include outputting the audible signal in conjunction with the presentation of the first user interface element at the first display device.

In some examples, the output signal data may include raw electrical signal data. In this example, the second user interface element may include a first representation of the raw electrical signal data a second representation of a processed portion of the raw electrical signal data.

The neurophysiological monitoring system described herein improves upon conventional systems for monitoring users that provide the same information to two displays associated with two users (e.g., a surgeon and a technologist). This is achieved, at least in part, by the system selectively determining which information (e.g., which user interface elements) to display on the two displays based on roles given to the users. Thus, although the underlying neurophysiological signals may be the same, the user interface elements displayed on both screens may be different. This improves the system by providing for more efficient operation of the system by requiring fewer click-throughs, screens, prompts, etc. to get to the most relevant data. Additionally, computing resources are conserved because the neurophysiological signal need only be captured and evaluated by one device, not two. Additionally, bandwidth may be conserved as the data being transferred to a secondary display may be much smaller as compared to the data being transferred to a primary display.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated examples thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed examples (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate examples of the disclosure and does not pose a limitation on the scope of the disclosure unless otherwise claimed. No language in the specification should be construed as indicating any non-claimed element as essential to the practice of the disclosure.

Preferred examples of this disclosure are described herein, including the best mode known to the inventors for carrying out the disclosure. Variations of those preferred examples may become apparent to those of ordinary skill in the art upon reading the foregoing description. The inventors expect skilled artisans to employ such variations as appropriate and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system, comprising:

a controller comprising interfaces for connecting with one or more attachment devices and an electrical stimulator, wherein the one or more attachment devices comprise electrodes, the controller configured to:

generate a stimulation signal that is deliverable to a subject via the one or more attachment devices; and receive neurological signal data via the one or more attachment devices, the neurological signal data generated at least in part by the subject in response to the stimulation signal being delivered to the subject;

a first display device positionable at a first position adjacent to the subject such that the first display device is viewable by a first user and a second user when positioned at the first position, the first display device configured to present a first user interface view comprising a first plurality of areas including a view area of the first plurality of areas to display a first representation of the neurological signal data and a second area of the first plurality of areas to display a graphical depiction of a representative human nervous system and one or more graphical indicators corresponding to a real-time neurological monitoring session;

a second display device positionable at a second position offset from the subject such that the second display device is viewable by the second user and obscured from the first user when positioned at the second position, the second display device configured to present a second user interface view comprising a second plurality of areas including a first area of the second plurality of areas to display a second representation of the neurological signal data and a second area of the second plurality of areas to display the graphical depiction of the representative human nervous system and the one or more graphical indicators corresponding to the real-time neurological monitoring session, the first user different from the second user at least with respect to respective responsibilities to the subject, wherein the first user interface view is distinct from the second user interface view; and a computing device electronically coupled with the controller and the first and second display devices, the computing device comprising a memory and a processor configured to:
  generate the first representation of the neurological signal data and the second representation of the neurological signal data;
  generate the graphical depiction of the representative human nervous system and the one or more graphical indicators corresponding to the real-time neurological monitoring session, wherein the one or more graphical indicators comprise a set of graphical indicators that is configured to represent electrode placement locations with respect to the subject and at least one attention graphical indicator that is configured to selectively identify locations of interest with respect to the subject;
  send the first representation of the neurological signal data and the graphical depiction of the representative human nervous system to the first display device for presentation to the first user; and
  send the second representation of the neurological signal data and the graphical depiction of the representative human nervous system to the second display device for presentation to the second user.

2. The system of claim 1, wherein the computer device is further configured to generate a first user interface element corresponding to the first representation of the neurological signal data and a second user interface element corresponding to the second representation of the neurological signal data.

3. The system of claim 2, wherein:
sending the first representation of the neurological signal data comprises sending the first user interface element corresponding to the first representation of the neurological signal data; and
sending the second representation of the neurological signal data comprises sending the second user interface element corresponding to the second representation of the neurological signal data.

4. The system of claim 1, wherein:
an action taken by the first user causes a change to at least one of the stimulation signal or the neurological signal data; and
generating the first representation of the neurological signal data is based at least in part on the change.

5. The system of claim 1, wherein:
the system further comprises:
  a bed configured to support the subject; and
  a table configured to support the computing device;
the first position is located adjacent the bed; and
the second position is located on the table.

6. The system of claim 1, wherein:
the first plurality of areas further comprises a comment field and a first message field;
the comment field is configurable to log user comments regarding the real-time neurological monitoring session; and
and the first message field is configurable to send to and receive messages from a second message field of the second plurality of areas.

7. An architecture for neurophysiological monitoring of a human subject, the architecture comprising:
a monitoring system comprising a controller and a computer, the monitoring system being configured to employ one or more electrophysiological modalities to monitor neural structures of the human subject when a surgical operation is performed on the human subject; and
a display system comprising:
  a first display device configured to be positioned at a first position adjacent to the human subject such that the first display device is viewable by a first user when the first user is performing the surgical operation on the human subject and viewable by a second user, the first display device configured to present a first user interface view comprising a first plurality of areas including:
    a first area of the first plurality of areas configured to display a first representation of first monitoring data based on data output by the monitoring system; and
    a second area of the first plurality of areas configured to display a graphical depiction of a representative human nervous system and one or more graphical indicators corresponding to monitoring of the neural structures of the human subject; and
  a second display device configured to be positioned at a second position offset from the human subject such that the second display device is viewable by the second user and obscured from the first user when the first user is performing the surgical operation on the human subject, the second display device configured to present a second user interface view comprising a second plurality of areas including:
    a first area of the second plurality of areas configured to display a second representation of second monitoring data based on data output by the monitoring system; and
    a second area of the second plurality of areas configured to display the graphical depiction of the representative human nervous system and one or more graphical indicators corresponding to monitoring of the neural structures of the human subject, wherein the one or more graphical indicators comprise a set of graphical indicators that is configured to represent electrode placement locations with respect to the human subject and at least one attention graphical indicator that is configured to selectively identify locations of interest with respect to the human subject.

8. The architecture of claim 7, wherein the one or more electrophysiological modalities comprise one or more of evoked potential monitoring, electromyography, or electroencephalography.

9. The architecture of claim 7, wherein:
the controller is configured to:
  generate first electrical signals for delivery to the neural structures of the human subject; and
  receive second electrical signals from the neural structures of the human subject; and
the computer is electronically coupled with the controller and the display system, the computer comprising a memory and a processor configured to:
  generate the first monitoring data based at least in part on the second electrical signals;
  generate the second monitoring data based at least in part on the second electrical signals; and
  provide at least one of the first monitoring data or the second monitoring data to at least one of the first display device or the second display device.

10. The architecture of claim 9, wherein generating the first monitoring data and the second monitoring data comprises generating a first user interface element that represents a first aspect of the second electrical signals and a second user interface element that represents a second aspect of the second electrical signals.

11. The architecture of claim 9, further comprising:
   a bed configured to support the human subject; and
   a table configured to support the computer.

12. The architecture of claim 11, wherein:
   the first position is located adjacent the bed; and
   the second position is located on the table.

13. The architecture of claim 9, wherein the computer is further configured to:
   receive user input from the second user via an input device; and
   provide a representation of the user input for presentation on the second display device.

14. A computer-implemented method, comprising:
   instructing a controller to initiate an electrophysiological monitoring routine on a nervous system of a patient, a controller comprising interfaces for connecting with one or more attachment devices and an electrical stimulator, the one or more attachment devices comprising electrodes;
   instructing the controller to generate a stimulation signal deliverable to the patient via the one or more attachment devices, wherein the controller is configured to receive neurological signal data via the one or more attachment devices, the neurological signal data generated at least in part by the patient in response to the stimulation signal being delivered to the patient;
   receiving output signal data from the controller, the output signal data comprising at least one of a triggered electrophysiological signal detected at the nervous system of the patient or a spontaneous electrophysiological signal detected at the nervous system of the patient;
   generating a plurality of user interface elements based at least in part on the output signal data, the plurality of user interface elements comprising a first representation of the output signal data and a second representation of the neurological signal data;
   generate a graphical depiction of a representative human nervous system and one or more graphical indicators corresponding to the electrophysiological monitoring routine, wherein the one or more graphical indicators comprise a set of graphical indicators that is configured to represent electrode placement locations with respect to the patient and at least one attention graphical indicator that is configured to selectively identify locations of interest with respect to the patient;
   providing a first user interface view for presentation at a first display device, first display device positioned at a first position such that a first user can view the first display device while physically interacting with the patient, the first user interface view comprising a first plurality of areas including:
      a first area of the first plurality of areas configured to display the first representation of the output signal data; and
      a second area of the first plurality of areas configured to display the graphical depiction of a representative human nervous system and the one or more graphical indicators; and
   providing a second user interface view for presentation at a second display device, the second display device positioned at a second position such that a second user can view the second display device and view the first display device, the second user interface view comprising a second plurality of areas including:
      a first area of the second plurality of areas configured to display the second representation of the output signal data; and
      a second area of the second plurality of areas configured to display the graphical depiction of the representative human nervous system and the one or more graphical indicators.

15. The computer-implemented method of claim 14, further comprising:
   generating an audible signal based at least in part on the output signal data; and
   outputting the audible signal in conjunction with the presentation of the first user interface view at the first display device.

16. The computer-implemented method of claim 14, wherein the output signal data comprises raw electrical signal data.

17. The computer-implemented method of claim 14, wherein the second position is located with respect to the patient in a manner that prohibits the second user from physically interacting with the patient.

* * * * *